US011800967B2

(12) United States Patent
Kitamura et al.

(10) Patent No.: US 11,800,967 B2
(45) Date of Patent: Oct. 31, 2023

(54) ENDOSCOPIC IMAGE PROCESSING APPARATUS, ENDOSCOPIC IMAGE PROCESSING METHOD, AND RECORDING MEDIUM RECORDING PROGRAM

(71) Applicant: OLYMPUS CORPORATION, Tokyo (JP)

(72) Inventors: Makoto Kitamura, Hachioji (JP); Yamato Kanda, Hino (JP); Katsuyoshi Taniguchi, Hino (JP)

(73) Assignee: OLYMPUS CORPORATON, Tokyo (JP)

(*) Notice: Subject to any disclaimer, the term of this patent is extended or adjusted under 35 U.S.C. 154(b) by 532 days.

(21) Appl. No.: 17/167,328

(22) Filed: Feb. 4, 2021

(65) Prior Publication Data

US 2021/0153721 A1    May 27, 2021

Related U.S. Application Data

(63) Continuation of application No. PCT/JP2018/034024, filed on Sep. 13, 2018.

(51) Int. Cl.
*A61B 1/00* (2006.01)
*G06N 20/00* (2019.01)

(52) U.S. Cl.
CPC ........ *A61B 1/00006* (2013.01); *A61B 1/0005* (2013.01); *A61B 1/000094* (2022.02);
(Continued)

(58) Field of Classification Search
CPC .......... A61B 1/00006; A61B 1/000094; A61B 1/000095; A61B 1/000096; A61B 1/0005; G06N 20/00
See application file for complete search history.

(56) References Cited

U.S. PATENT DOCUMENTS

2018/0047163 A1* 2/2018 Kanda ..................... G06T 7/246
2018/0096191 A1    4/2018 Wan et al.
(Continued)

FOREIGN PATENT DOCUMENTS

JP    2004-073488 A    3/2004
JP    2018-515164 A    6/2018
(Continued)

OTHER PUBLICATIONS

International Search Report dated Nov. 13, 2018 received in PCT/JP2018/034024.

*Primary Examiner* — David Bilodeau
(74) *Attorney, Agent, or Firm* — Scully, Scott, Murphy & Presser, P.C.

(57) ABSTRACT

An endoscopic image processing apparatus includes a processor having a lesion recognizing function capable of recognizing a lesioned part included in an image generated by applying predetermined processing. The processor has the lesion recognizing function implemented by performing machine learning using, as a plurality of learning images, a plurality of past observation images generated through the predetermined processing, and the processor performs conversion processing for converting, based on a setting value for learning image equivalent to a past setting value for observation image used in the predetermined processing performed at generation of each of the plurality of learning images, the image into an image for lesion recognition used for processing corresponding to the lesion recognizing function.

14 Claims, 8 Drawing Sheets

(52) U.S. Cl.
CPC .. *A61B 1/000095* (2022.02); *A61B 1/000096* (2022.02); *G06N 20/00* (2019.01)

(56) References Cited

U.S. PATENT DOCUMENTS

| | | | | |
|---|---|---|---|---|
| 2019/0200905 | A1* | 7/2019 | Shelton, IV | A61B 1/044 |
| 2020/0138265 | A1* | 5/2020 | Endo | A61B 1/000094 |
| 2020/0146529 | A1* | 5/2020 | Kono | G06T 7/0012 |
| 2020/0342267 | A1* | 10/2020 | Usuda | G06V 10/82 |

FOREIGN PATENT DOCUMENTS

| | | |
|---|---|---|
| WO | 2016/160491 A1 | 10/2016 |
| WO | 2016/170655 A1 | 10/2016 |
| WO | 2018/008593 A1 | 1/2018 |

\* cited by examiner

ENDOSCOPIC IMAGE PROCESSING APPARATUS, ENDOSCOPIC IMAGE PROCESSING METHOD, AND RECORDING MEDIUM RECORDING PROGRAM

CROSS REFERENCE TO RELATED APPLICATION

This application is a continuation application of PCT/JP2018/034024 filed on Sep. 13, 2018, the entire contents of which are incorporated herein by this reference.

BACKGROUND OF THE INVENTION

1. Field of the Invention

The present invention relates to an endoscopic image processing apparatus, an endoscopic image processing method, and a recording medium recording a program.

2. Description of the Related Art

In a medical field, there has been known a technique for detecting a lesioned part from an image obtained by picking up an image of a desired site of a subject, adding information concerning the detected lesioned part to the image, and displaying the information.

More specifically, for example, Japanese Patent Application Laid-Open Publication No. 2004-73488 discloses a technique for detecting a lesioned part from an X-ray image obtained by picking up an image of a chest of a subject and displaying, in an outer frame portion of a diagnostic image corresponding to the X-ray image, a mark capable of specifying a position of the detected lesioned part.

In the medical field, in recent years, for example, an examination has been performed concerning a method of performing machine learning based on a plurality of images obtained by picking up an image of an inside of a body of a subject with an endoscope to thereby create a recognizer having a lesion recognizing function capable of recognizing a lesioned part such as a tumor and performing an actual endoscopic observation using the created recognizer.

SUMMARY OF THE INVENTION

An endoscopic image processing apparatus according to an aspect of the present invention is an endoscopic image processing apparatus to which an image generated by applying predetermined processing to an image pickup signal obtained by picking up an image of an object in a subject with an endoscope is inputted from an external apparatus, the endoscopic image processing apparatus having a lesion recognizing function capable of recognizing a lesioned part included in the inputted image, the endoscopic image processing apparatus including a processor, the processor having the lesion recognizing function implemented by performing machine learning using, as a plurality of learning images, a plurality of past observation images generated through the predetermined processing, the processor performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

An endoscopic image processing method according to an aspect of the present invention is an endoscopic image processing method in an endoscopic image processing apparatus to which an image generated by applying predetermined processing to an image pickup signal obtained by picking up an image of an object in a subject with an endoscope is inputted from an external apparatus, the endoscopic image processing apparatus having a lesion recognizing function capable of recognizing a lesioned part included in the inputted image, the endoscopic image processing method including: performing machine learning for implementing the lesion recognizing function using, as a plurality of learning images, a plurality of past observation images generated through the predetermined processing; and performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

A non-transitory computer-readable recording medium recording a program according to an aspect of the present invention is a recording medium recording a program to be executed by a computer to which an image generated by applying predetermined processing to an image pickup signal obtained by picking up an image of an object in a subject with an endoscope is inputted from an external apparatus, the computer having a lesion recognizing function capable of recognizing a lesioned part included in the inputted image, the recording medium recording a program for causing the computer to execute: a step of performing machine learning for implementing the lesion recognizing function using, as a plurality of learning images, a plurality of past observation images generated through the predetermined processing; and a step of performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

DETAILED DESCRIPTION OF THE PREFERRED EMBODIMENTS

Embodiments of the present invention are explained below with reference to the drawings.

First Embodiment

Figure 1:
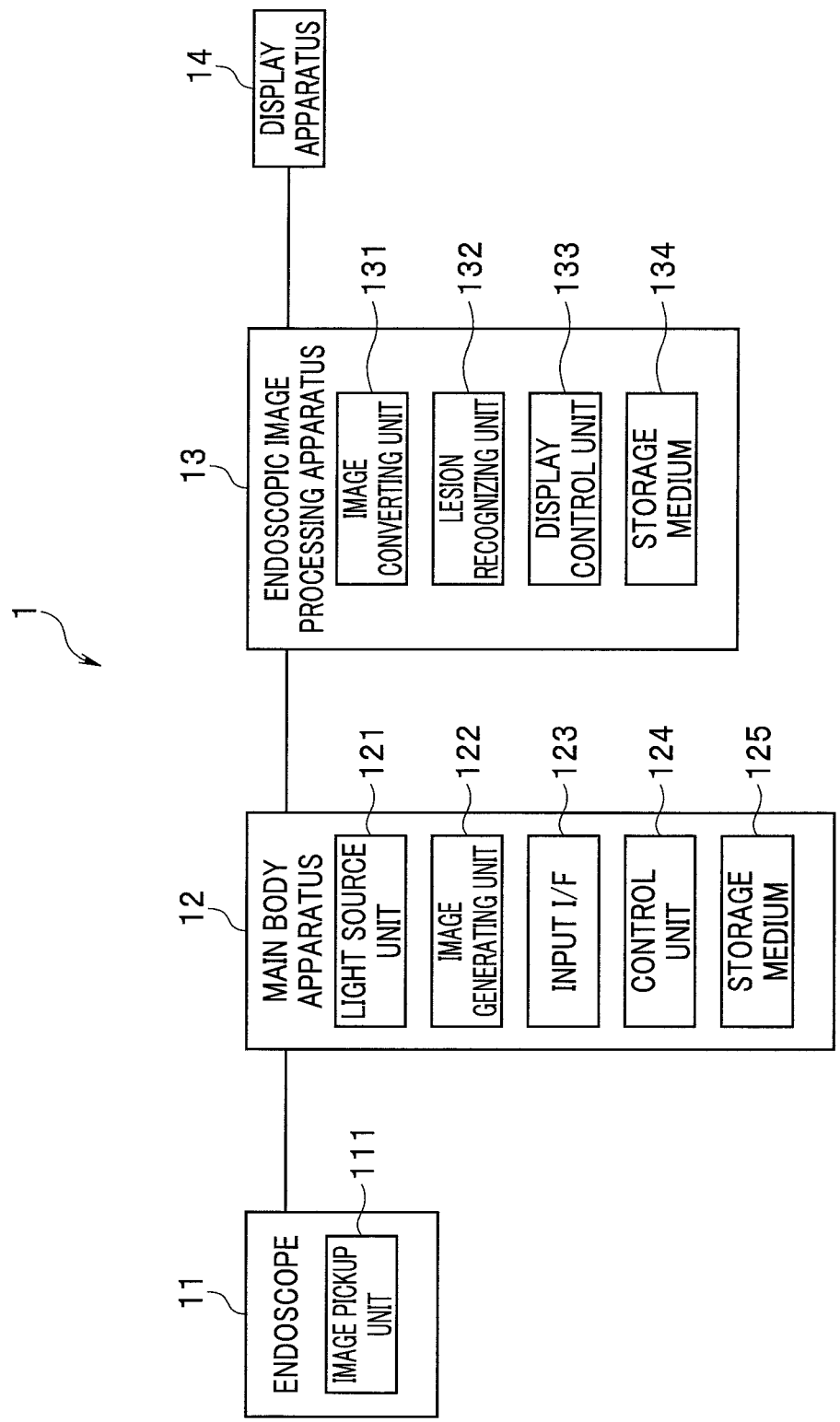
FIG. 1 is a diagram showing a configuration of a main part of an endoscope system including an endoscopic image processing apparatus according to a first embodiment.
Figure 2:
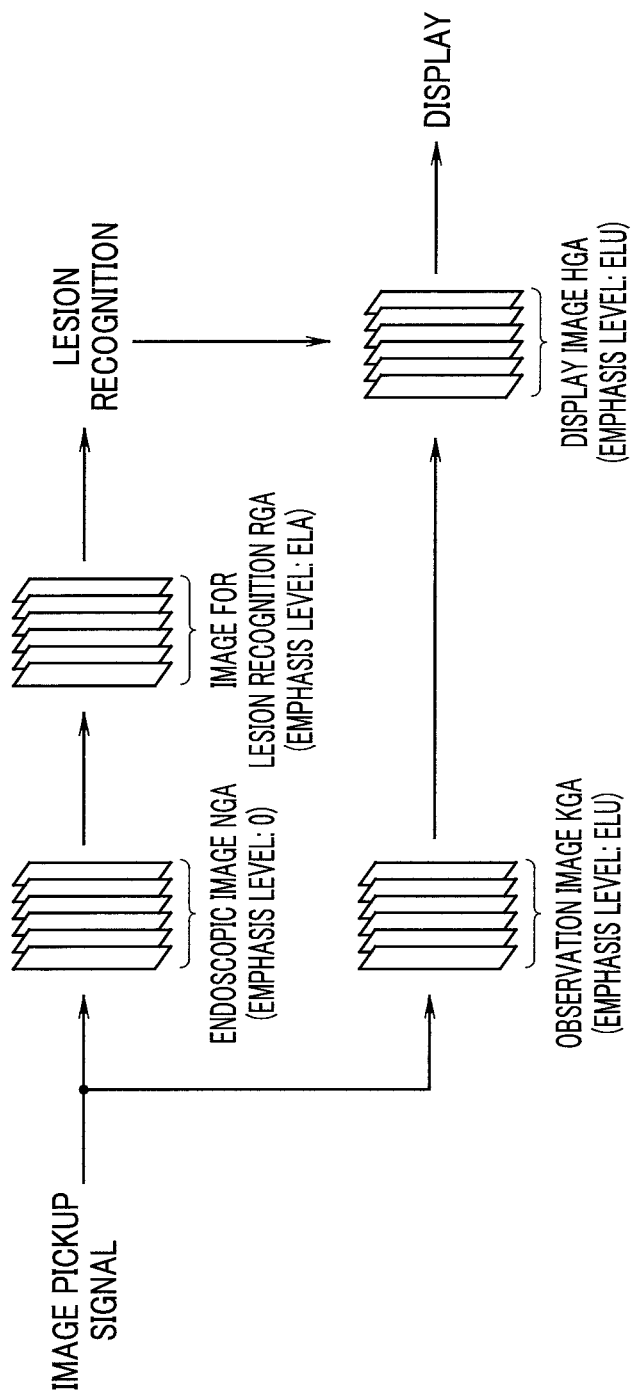
FIG. 2 is a diagram showing an overview of operation performed in the endoscopic image processing apparatus and the like according to the first embodiment.

FIG. 1 and FIG. 2 relate to a first embodiment of the present invention.

An endoscope system 1 includes, as shown in FIG. 1, an endoscope 11, a main body apparatus 12, an endoscopic image processing apparatus 13, and a display apparatus 14. FIG. 1 is a diagram showing a configuration of a main part of an endoscope system including an endoscopic image processing apparatus according to the first embodiment.

The endoscope 11 includes, for example, an insertion section (not illustrated) having an elongated shape insertable into a subject and an operation section (not illustrated) provided at a proximal end portion of the insertion section. The endoscope 11 is detachably connected to the main body apparatus 12 via, for example, a universal cable (not illustrated) extending from the operation section. For example, a light guide member (not illustrated) such as an optical fiber for guiding illumination light supplied from the main body apparatus 12 and emitting the illumination light from a distal end portion of the insertion section is provided on an inside of the endoscope 11. An image pickup unit 111 is provided at the distal end portion of the insertion section of the endoscope 11.

The image pickup unit 111 includes, for example, an image pickup device such as a CCD image sensor or a CMOS image sensor. The image pickup unit 111 is configured to pick up an image of return light from an object illuminated by the illumination light emitted through the distal end portion of the insertion section of the endoscope 11, generate an image pickup signal corresponding to the return light, the image of which is picked up, and output the image pickup signal to the main body apparatus 12.

The main body apparatus 12 is detachably connected to each of the endoscope 11 and the endoscopic image processing apparatus 13. The main body apparatus 12 includes, for example, as shown in FIG. 1, a light source unit 121, an image generating unit 122, an input I/F (interface) 123, a control unit 124, and a storage medium 125.

The light source unit 121 includes, for example, one or more light emitting elements such as LEDs. More specifically, the light source unit 121 includes, for example, a blue LED that generates blue light (hereinafter referred to as B light as well), a green LED that generates green light (hereinafter referred to as G light as well), and a red LED that generates red light (hereinafter referred to as R light as well). The light source unit 121 is configured to be able to generate illumination light corresponding to control by the control unit 124 and supply the illumination light to the endoscope 11.

The image generating unit 122 is configured to generate an endoscopic image by reading a default setting value (set in advance during factory shipment) stored in the storage medium 125 and applying predetermined processing to an image pickup signal outputted from the endoscope 11 using the read setting value. The image generating unit 122 is configured to generate an observation image by reading a setting value for present observation image stored in the storage medium 125 and applying the predetermined processing to an image pickup signal outputted from the endoscope 11 using the read setting value. The image generating unit 122 is configured to, when detecting that the setting value for present observation image is not stored in the storage medium 125, generate the observation image using, as the setting value for present observation image, the default setting value read from the storage medium 125. The image generating unit 122 is configured to output both of the endoscopic image and the observation image generated as explained above to the endoscopic image processing apparatus 13. Note that, in the present embodiment, the predetermined processing performed by the image generating unit 122 only has to include one or more kinds of processing in which a setting value can be changed by a user.

In the input I/F 123, one or more switches with which an instruction corresponding to input operation by the user can be given to the control unit 124 are provided. In the input I/F 123, for example, a switch with which an instruction for setting the setting value for present observation image used in the processing of the image generating unit 122 to a desired value can be performed is provided.

The control unit 124 is configured to perform, based on an instruction or the like performed in the input I/F 123, control relating to operations of the respective sections of the endoscope 11 and the main body apparatus 12. The control unit 124 is configured to, when detecting that the instruction for setting the setting value for present observation image used in the processing of the image generating unit 122 to a desired value is performed, perform operation for updating, according to the instruction, the setting value stored in the storage medium 125.

The storage medium 125 includes, for example, a nonvolatile memory. The default setting value and the setting value for present observation image used in the processing of the image generating unit 122 are stored in the storage medium 125.

In the present embodiment, the image generating unit 122 and the control unit 124 of the main body apparatus 12 may be configured as individual electronic circuits or may be configured as circuit blocks in an integrated circuit such as an FPGA (field programmable gate array). In the present embodiment, for example, the main body apparatus 12 may include one or more processors such as CPUs. By modifying a configuration according to the present embodiment as appropriate, for example, a not-shown computer may read, from the storage medium 125, a program for causing the computer to execute the functions of the image generating unit 122 and the control unit 124 and may perform operation corresponding to the read program.

The endoscopic image processing apparatus 13 is detachably connected to each of the main body apparatus 12 and the display apparatus 14. The endoscopic image processing apparatus 13 is configured to receive, from the main body apparatus 12 (equivalent to an external apparatus), an input of an endoscopic image generated by applying predetermined processing to an image pickup signal obtained by picking up an image of an object in a subject with the endoscope 11. The endoscopic image processing apparatus 13 has a lesion recognizing function capable of recognizing a lesioned part included in the inputted endoscopic image. The endoscopic image processing apparatus 13 includes an image converting unit 131, a lesion recognizing unit 132, a display control unit 133, and a storage medium 134.

The image converting unit 131 is configured to read a setting value for learning image stored in the storage medium 134 and perform conversion processing for converting, using the read setting value, an endoscopic image outputted from the main body apparatus 12 into an image for lesion recognition. In other words, the image converting unit 131 is configured to perform conversion processing for converting the endoscopic image outputted from the main body apparatus 12 into an image for lesion recognition corresponding to the setting value for learning image read from the storage medium 134.

The lesion recognizing unit 132 has a lesion recognizing function capable of recognizing a lesioned part such as a tumor included in an image obtained by picking up an image of an inside of a body of a subject with the endoscope. The lesion recognizing unit 132 is configured to perform, as processing corresponding to the lesion recognizing function explained above, processing for detecting a lesioned part included in the image for lesion recognition obtained as a processing result of the image converting unit 131 and perform processing for acquiring information concerning the detected lesioned part. More specifically, the lesion recognizing unit 132 is configured to perform, for example, processing for acquiring, as the information concerning the lesioned part, at least one kind of information among a position, a size, malignancy of the lesioned part included in the image for lesion recognition obtained as the processing result of the image converting unit 131. The lesion recognizing function of the lesion recognizing unit 132 is a function implemented by performing machine learning such as deep learning using, as a learning image, each of a plurality of observation images acquired (recorded) during endoscopic observation in the past. In other words, the lesion recognizing unit 132 has a lesion recognizing function implemented by performing machine learning using, as a plurality of learning images, a plurality of past observation images generated through predetermined processing by the image generating unit 122.

The display control unit 133 is configured to generate a display image by combining the observation image outputted from the main body apparatus 12 and the information concerning the lesioned part obtained as the processing result of the lesion recognizing unit 132 and output the generated display image to the display apparatus 14. In other words, the display control unit 133 is configured to generate a display image by combining the observation image inputted from the main body apparatus 12 and the information concerning the lesioned part obtained by the lesion recognizing unit 132 applying the processing corresponding to the lesion recognizing function to the image for lesion recognition. The display control unit 133 is configured to, when information concerning the lesioned part is not obtained by the processing of the lesion recognizing unit 132, directly output the observation image outputted from the main body apparatus 12 to the display apparatus 14 as a display image.

The storage medium 134 includes, for example, a nonvolatile memory. In the storage medium 134, the setting value for learning image equivalent to the past setting value for observation image used for learning for implementing the lesion recognizing function of the lesion recognizing unit 132 is stored. In other words, the setting value for learning image stored in the storage medium 134 is equivalent to the past setting value for observation image used in the predetermined processing performed by the image generating unit 122 and set by the user at generation of each of the plurality of learning images.

In the present embodiment, the respective sections of the endoscopic image processing apparatus 13 may be configured as individual electronic circuits or may be configured as circuit blocks in an integrated circuit such as an FPGA (field programmable gate array). In the present embodiment, for example, the endoscopic image processing apparatus 13 may include one or more processors such as CPUs. By modifying the configuration according to the present embodiment as appropriate, for example, a not-shown computer may read, from the storage medium 134, a program for causing the computer to execute the functions of the image converting unit 131, the lesion recognizing unit 132, and the display control unit 133 and may perform operation corresponding to the read program.

The display apparatus 14 includes a monitor and is configured to be able to display a display image outputted through the endoscopic image processing apparatus 13.

Subsequently, action in the present embodiment is explained with reference to FIG. 2. FIG. 2 is a diagram showing an overview of operation performed in the endoscopic image processing apparatus and the like according to the first embodiment.

In the following explanation, unless particularly referred to otherwise, as an example, the B light, the G light, and the R light are sequentially or simultaneously emitted from the light source unit 121 as illumination light corresponding to the control by the control unit 124, that is, an image having color components of blue, green, and red is generated by the image generating unit 122.

In the present embodiment, it is assumed that respective observation images (learning images) used for the learning for implementing the lesion recognizing function of the lesion recognizing unit 132 are acquired by the endoscope system including the endoscope 11 and the main body apparatus 12.

In the present embodiment, as an example, contour emphasis processing for emphasizing a contour of an object, an image of which is picked up by the image pickup unit 111, is included in the predetermined processing performed by the image generating unit 122. In the explanation of the present embodiment, it is assumed that a setting value of the contour emphasis processing performed by the image generating unit 122 is represented as a plurality of emphasis levels to which numerical values 0 to P (P is an integer equal to or larger than 1) are allocated. In the explanation of the present embodiment, it is assumed that a switch or the like with which an instruction for setting an emphasis level of the contour emphasis processing performed by the image generating unit 122 to desired emphasis levels of 0 to P can be performed is provided in the input I/F 123.

In the present embodiment, as an example, a default emphasis level (setting value) ELD of the contour emphasis processing is stored in the storage medium 125 and the emphasis level ELD is set to 0. In the explanation of the present embodiment, when the emphasis level of the contour emphasis processing is set to 0, the contour of the object, the image of which is picked up by the image pickup unit 111, is not emphasized. In the explanation of the present embodiment, it is assumed that a positive correlation is present between the emphasis level of the contour emphasis processing and an emphasis state of the contour of the object, the image of which is picked up by the image pickup unit 111.

After connecting the respective sections of the endoscope system 1 and turning on a power supply, a user such as a surgeon inserts the insertion section of the endoscope 11 into an inside of a subject and disposes the distal end portion of the insertion section in a position where an image of a desired object can be picked up on the inside of the subject. According to such operation by the user, illumination light is supplied from the light source unit 121 to the endoscope 11 and an image of return light from the object illuminated by the illumination light is picked up by the image pickup unit 111, and an image pickup signal generated by the image pickup unit 111 is outputted to the main body apparatus 12.

The user operates the input I/F 123 to thereby perform, for example, an instruction for setting the emphasis level used in the contour emphasis processing of the image generating unit 122 to a desired emphasis level ELU. According to such operation by the user, the emphasis level (setting value) for present observation image stored in the storage medium 125 is updated to ELU.

The image generating unit 122 reads the default emphasis level ELD stored in the storage medium 125 and generates an endoscopic image NGA by applying predetermined processing (including the contour emphasis processing) to the image pickup signal outputted from the endoscope 11 using the read emphasis level ELD (=0) (see FIG. 2). In other words, the endoscopic image NGA is generated as an image in which the contour of the object, the image of which is picked up by the image pickup unit 111, is not emphasized.

The image generating unit 122 generates an observation image KGA by reading the emphasis level ELU for present observation image stored in the storage medium 125 and applying the predetermined processing (including the contour emphasis processing) to the image pickup signal outputted from the endoscope 11 using the read emphasis level ELU (see FIG. 2). In other words, the observation image KGA is generated as an image in which the contour of the object, the image of which is picked up by the image pickup unit 111, is emphasized according to the emphasis level ELU.

The image generating unit 122 outputs both of the endoscopic image NGA and the observation image KGA generated as explained above to the endoscopic image processing apparatus 13.

The image converting unit 131 reads an emphasis level ELA for learning image stored in the storage medium 134 and performs conversion processing for converting the endoscopic image NGA outputted from the main body apparatus 12 into an image for lesion recognition RGA using the read emphasis level ELA (see FIG. 2). In other words, the image for lesion recognition RGA is generated as an image in which a contour of an object included in the endoscopic image NGA is emphasized according to the emphasis level ELA.

The emphasis level ELA for learning image is equivalent to an emphasis level with the highest frequency of use among emphasis levels ELU set by the user in each of the plurality of past observation images used for the learning for implementing the lesion recognizing function of the lesion recognizing unit 132. In other words, the emphasis level ELA for learning image is equivalent to an emphasis level with the largest number of times of setting by the user among a plurality of emphasis levels used in the predetermined processing performed at generation of each of the plurality of learning images. Accordingly, with the conversion processing of the image converting unit 131 explained above, emphasis states of the contour of the object in the image for lesion recognition RGA generated according to the endoscopic image NGA obtained in the actual endoscopic observation and a learning image LGA used for the learning for implementing the lesion recognizing function of the lesion recognizing unit 132 can be made similar to each other.

The lesion recognizing unit 132 performs processing for detecting a lesioned part included in the image for lesion recognition RGA obtained as the processing result of the image converting unit 131 and performs processing for acquiring information concerning the detected lesioned part.

The display control unit 133 generates a display image HGA by combining the observation image KGA outputted from the main body apparatus 12 and the information concerning the lesioned part obtained as a processing result of the lesion recognizing unit 132 and outputs the generated display image HGA to the display apparatus 14 (see FIG. 2).

As explained above, according to the present embodiment, the image for lesion recognition RGA having the emphasis state similar to the emphasis state of the learning image LGA is generated by the conversion processing of the image converting unit 131. Processing relating to recognition of the lesioned part included in the generated image for lesion recognition RGA is performed by the lesion recognizing unit 132. Accordingly, according to the present embodiment, it is possible to suppress deterioration in recognition accuracy of a lesioned part that occurs because of a difference between acquisition conditions for an image used for machine learning and an image obtained in the actual endoscopic observation.

Note that, by modifying the configurations and/or the operations of the respective sections explained above as appropriate, the present embodiment can be applied to various kinds of processing in which the setting value for observation image can be changed by the user. More specifically, the present embodiment can also be applied to processing different from the contour emphasis processing such as color tone adjustment processing, chroma adjustment processing, and brightness adjustment processing.

Second Embodiment

Figure 3:
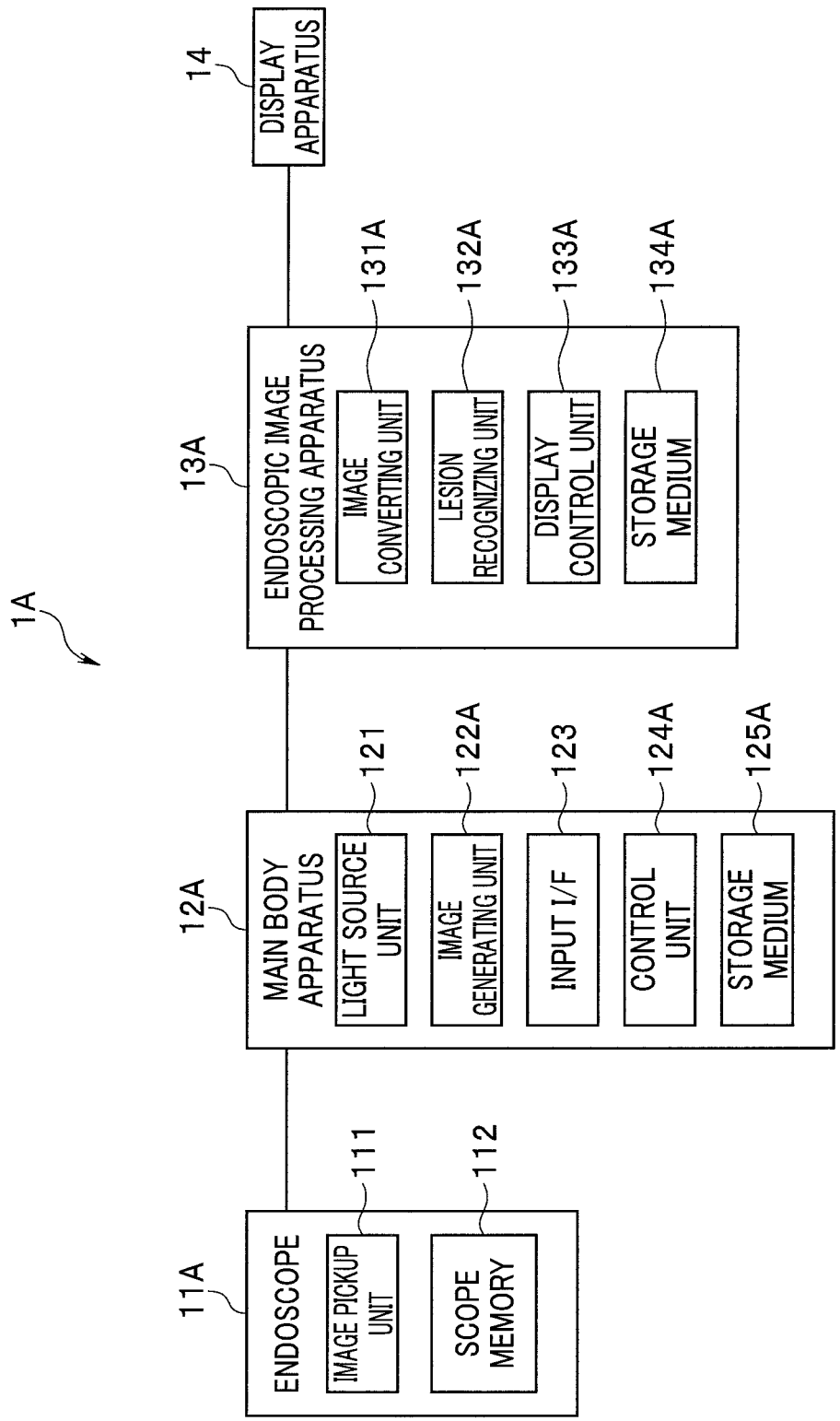
FIG. 3 is a diagram showing a configuration of a main part of an endoscope system including an endoscopic image processing apparatus according to a second embodiment.
Figure 4:
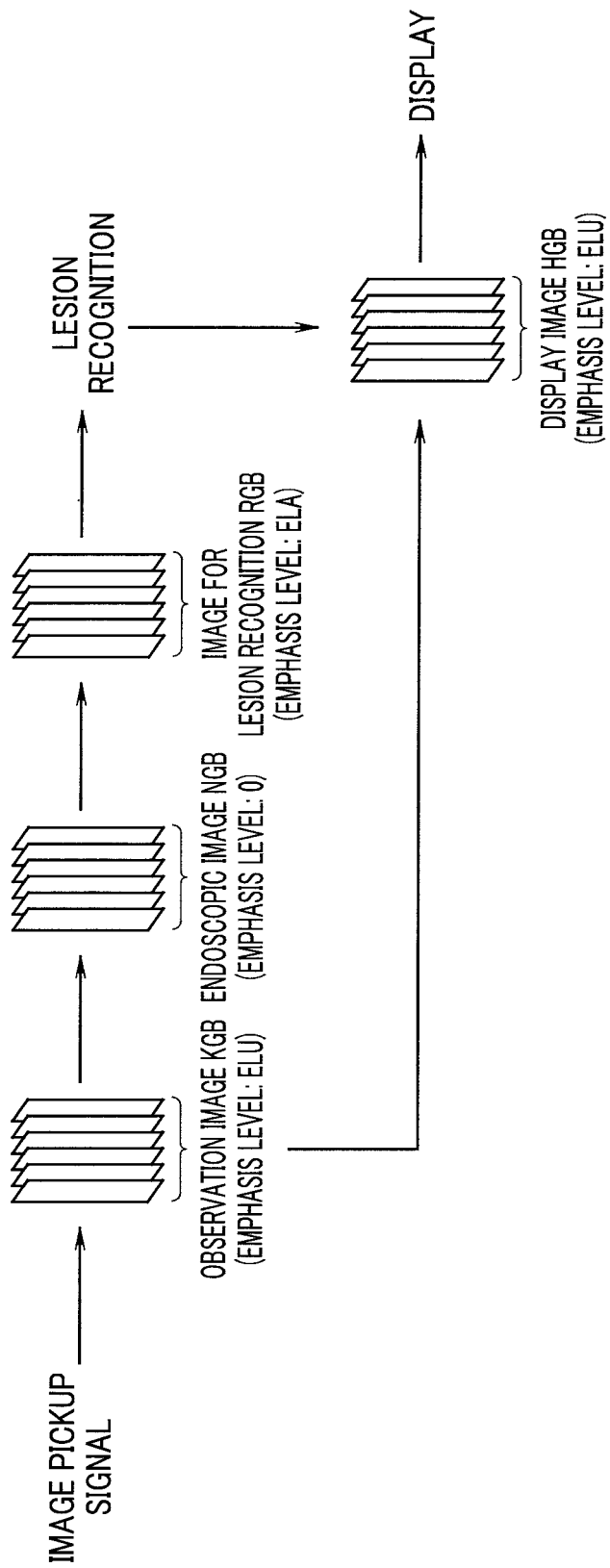
FIG. 4 is a diagram showing an overview of operation performed in the endoscopic image processing apparatus and the like according to the second embodiment.
Figure 5:
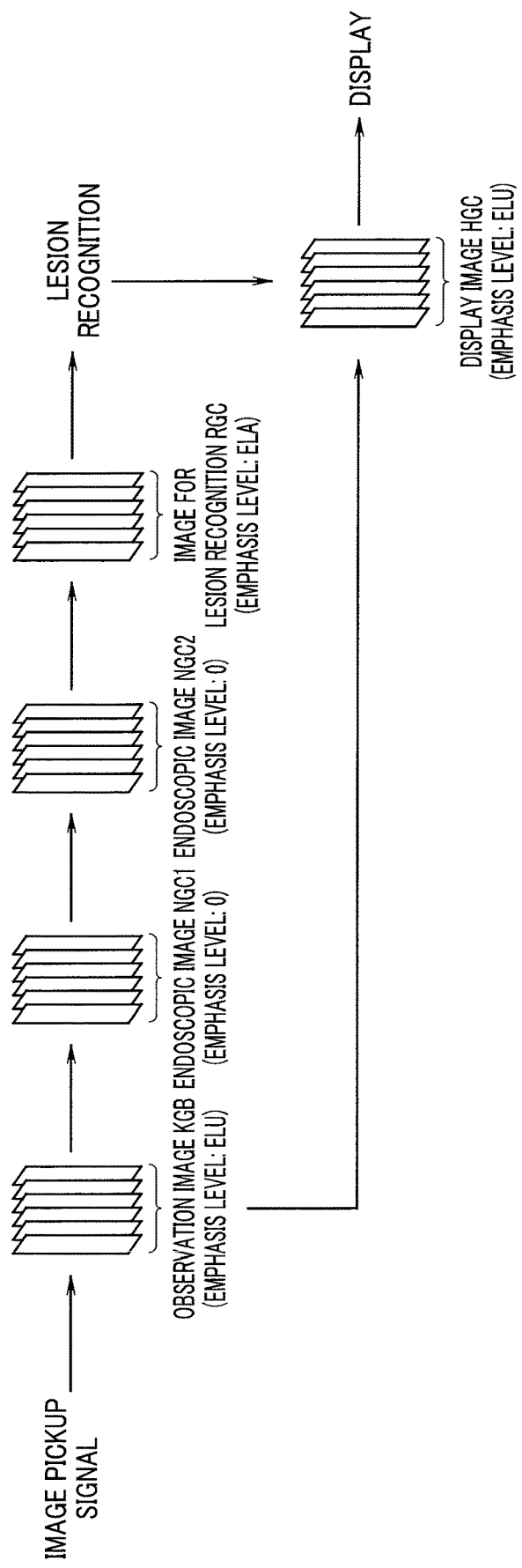
FIG. 5 is a diagram showing an overview of operation performed in the endoscopic image processing apparatus and the like according to the second embodiment.

FIG. 3 to FIG. 5 relate to a second embodiment of the present invention.

Note that, in the present embodiment, detailed explanation concerning portions having the same configurations and the like as the configuration and the like in the first embodiment is omitted as appropriate and portions having configurations and the like different from the configurations and the like in the first embodiment are mainly explained.

An endoscope system 1A includes, as shown in FIG. 3, an endoscope 11A, a main body apparatus 12A, an endoscopic image processing apparatus 13A, and the display apparatus 14. FIG. 3 is a diagram showing a configuration of a main part of an endoscope system including an endoscopic image processing apparatus according to the second embodiment.

The endoscope 11A includes, for example, an insertion section (not illustrated) having an elongated shape insertable into a subject and an operation section (not illustrated) provided at a proximal end portion of the insertion section. The endoscope 11A is detachably connected to the main body apparatus 12A via, for example, a universal cable (not illustrated) extending from the operation section. For example, a light guide member (not illustrated) such as an optical fiber for guiding illumination light supplied from the main body apparatus 12A and emitting the illumination light from a distal end portion of the insertion section is provided on an inside of the endoscope 11A. The endoscope 11A includes the image pickup unit 111 and a scope memory 112.

For example, endoscopic information including information capable of specifying a model of the endoscope 11A is stored in the scope memory 112. Note that the model of the endoscope 11A included in the endoscopic information is set based on, for example, the number of effective pixels of an image sensor provided in the image pickup unit 111.

The main body apparatus 12A is detachably connected to each of the endoscope 11A and the endoscopic image processing apparatus 13A. The main body apparatus 12A includes, for example, as shown in FIG. 3, the light source unit 121, an image generating unit 122A, the input I/F 123, a control unit 124A, and a storage medium 125A.

The image generating unit 122A is configured to generate an observation image by reading a setting value for present observation image stored in the storage medium 125A and applying predetermined processing to an image pickup signal outputted from the endoscope 11A using the read setting value. The image generating unit 122A is configured to, when detecting that the setting value for present observation image is not stored in the storage medium 125A, generate the observation image using, as the setting value for present observation image, a default setting value read from the storage medium 125A. The image generating unit 122A is configured to output both of the observation image generated as explained above and the setting value for present observation image used for the generation of the observation image to the endoscopic image processing apparatus 13A. Note that, in the present embodiment, the predetermined processing performed by the image generating unit 122A only has to include one or more kinds of processing in which a setting value can be changed by a user.

The control unit 124A is configured to perform, based on an instruction or the like performed in the input I/F 123, control relating to operations of the respective sections of the endoscope 11A and the main body apparatus 12A. The control unit 124A is configured to, when detecting that the instruction for setting the setting value for present observation image used in the processing of the image generating unit 122A to a desired value is performed, perform operation for updating, according to the instruction, the setting value stored in the storage medium 125A. The control unit 124A is configured to, when a power supply of the main body apparatus 12A is turned on, read the endoscopic information stored in the scope memory 112 and main body apparatus information stored in the storage medium 125A and output both of the read endoscopic information and the read main body apparatus information to the endoscopic image processing apparatus 13A.

The storage medium 125A includes, for example, a non-volatile memory. In the storage medium 125A, the default setting value and the setting value for present observation image used in the processing of the image generating unit 122A are stored. In the storage medium 125A, main body apparatus information including information capable of specifying a model of the main body apparatus 12A is stored. Note that the model of the main body apparatus 12A included in the main body apparatus information is set based on, for example, kinds of colors of lights emitted from the respective LEDs provided in the light source unit 121.

In the present embodiment, the image generating unit 122A and the control unit 124A of the main body apparatus 12A may be configured as individual electronic circuits or may be configured as circuit blocks in an integrated circuit such as an FPGA (field programmable gate array). In the present embodiment, for example, the main body apparatus 12A may include one or more processors such as CPUs. By modifying a configuration according to the present embodiment as appropriate, for example, a not-shown computer may read, from the storage medium 125A, a program for causing the computer to execute the functions of the image generating unit 122A and the control unit 124A and may perform operation corresponding to the read program.

The endoscopic image processing apparatus 13A is detachably connected to each of the main body apparatus 12A and the display apparatus 14. The endoscopic image processing apparatus 13A is configured to receive, from the main body apparatus 12A, an input of an observation image generated by applying predetermined processing to an image pickup signal obtained by picking up an image of an object in a subject with the endoscope 11A. The endoscopic image processing apparatus 13A has a lesion recognizing function capable of recognizing a lesioned part included in the inputted observation image. The endoscopic image processing apparatus 13A includes an image converting unit 131A, a lesion recognizing unit 132A, a display control unit 133A, and a storage medium 134A.

The image converting unit 131A is configured to detect models of the endoscope 11A and the main body apparatus 12A based on the endoscopic information and the main body apparatus information outputted from the main body apparatus 12A. The image converting unit 131A is configured to perform conversion processing for converting, based on the models of the endoscope 11A and the main body apparatus 12A detected as explained above, the setting value for present observation image outputted from the main body apparatus 12A, and the setting value for learning image read from the storage medium 134A, the observation image outputted from the main body apparatus 12A into an image for lesion recognition.

The lesion recognizing unit 132A has a lesion recognizing function implemented by performing machine learning with the same method as the method of the lesion recognizing unit 132. The lesion recognizing unit 132A is configured to perform, as processing corresponding to the lesion recognizing function, processing for detecting a lesioned part included in the image for lesion recognition obtained as a processing result of the image converting unit 131A and perform processing for acquiring information concerning the detected lesioned part. In other words, the lesion recognizing unit 132A has a lesion recognizing function implemented by performing machine learning using, as a plurality of learning images, a plurality of past observation images generated through the predetermined processing by the image generating unit 122A.

The display control unit 133A is configured to generate a display image by combining the observation image outputted from the main body apparatus 12A and the information concerning the lesioned part obtained as the processing result of the lesion recognizing unit 132A and output the generated display image to the display apparatus 14. In other words, the display control unit 133A is configured to generate a display image by combining the observation image inputted from the main body apparatus 12A and the information concerning the lesioned part obtained by the lesion recognizing unit 132A applying the processing corresponding to the lesion recognizing function to the image for lesion recognition. The display control unit 133A is configured to, when information concerning the lesioned part is not obtained by the processing of the lesion recognizing unit 132A, directly output the observation image outputted from the main body apparatus 12A to the display apparatus 14 as a display image.

The storage medium 134A includes, for example, a non-volatile memory. In the storage medium 134A, the setting value for learning image equivalent to the past setting value for observation image used for learning for implementing the lesion recognizing function of the lesion recognizing unit 132A is stored. In other words, the setting value for learning image stored in the storage medium 134A is equivalent to the past setting value for observation image used in the predetermined processing performed by the image generating unit 122A and set by the user at generation of each of the plurality of learning images. In the storage medium 134A, a default setting value and a plurality of conversion matrixes used in the conversion processing of the image converting unit 131A are stored.

The default setting value is set as a value corresponding to the model of the main body apparatus 12A and is set as a value corresponding to the predetermined processing performed by the image generating unit 122A. The plurality of conversion matrixes are set as matrixes for performing conversion of a color tone and resolution according to the models of the endoscope 11A and the main body apparatus 12A. Respective coefficients included in the plurality of conversion matrixes are set according to, for example, the number of effective pixels of the image sensor of the image pickup unit 111 and kinds of colors of lights emitted from the respective LEDs provided in the light source unit 121.

In the present embodiment, the respective sections of the endoscopic image processing apparatus 13A may be configured as individual electronic circuits or may be configured as circuit blocks in an integrated circuit such as an FPGA (field programmable gate array). In the present embodiment, for example, the endoscopic image processing apparatus 13A may include one or more processors such as CPUs. By modifying the configuration according to the present embodiment as appropriate, for example, a not-shown computer may read, from the storage medium 134A, a program for causing the computer to execute the functions of the image converting unit 131A, the lesion recognizing unit 132A, and the display control unit 133A and may perform operation corresponding to the read program.

Subsequently, action in the present embodiment is explained with reference to FIG. 4 and FIG. 5. FIG. 4 and FIG. 5 are diagrams showing an overview of operation performed in the endoscopic image processing apparatus and the like according to the second embodiment.

In the present embodiment, as an example, respective observation images (learning images) used for the learning for implementing the lesion recognizing function of the lesion recognizing unit 132A are acquired by an endoscope system including an endoscope of a model EMA and a main body apparatus of a model HMA.

In the present embodiment, as an example, the same contour emphasis processing as the contour emphasis processing of the image generating unit 122 is performed by the image generating unit 122A. In the explanation of the present embodiment, it is assumed that a setting value of the contour emphasis processing performed by the image generating unit 122A is represented as a plurality of emphasis levels to which numerical values 0 to P (P is an integer equal to or larger than 1) are allocated.

In the present embodiment, as an example, the default emphasis level (setting value) ELD of the contour emphasis processing is stored in the storage media 125A and 134A and the emphasis level ELD is set to 0.

After connecting the respective sections of the endoscope system 1A and turning on a power supply, a user such as a surgeon inserts the insertion section of the endoscope 11A into an inside of a subject and disposes the distal end portion of the insertion section in a position where an image of a desired object can be picked up on the inside of the subject. According to such operation by the user, illumination light is supplied from the light source unit 121 to the endoscope 11A and an image of return light from the object illuminated by the illumination light is picked up by the image pickup unit 111, and an image pickup signal generated by the image pickup unit 111 is outputted to the main body apparatus 12A.

The user operates the input I/F 123 to thereby perform, for example, an instruction for setting the emphasis level used in the contour emphasis processing of the image generating unit 122 to the desired emphasis level ELU. According to such operation by the user, the emphasis level (setting value) for present observation image stored in the storage medium 125 is updated to ELU.

When the power supply of the main body apparatus 12A is turned on, the control unit 124A reads endoscopic information EJB stored in the scope memory 112 and main body apparatus information HJB stored in the storage medium 125A and outputs both of the read endoscopic information EJB and the read main body apparatus information HJB to the endoscopic image processing apparatus 13A.

The image generating unit 122A generates an observation image KGB by reading the emphasis level ELU for present observation image stored in the storage medium 125 and applying predetermined processing (including the contour emphasis processing) to an image pickup signal outputted from the endoscope 11A using the read emphasis level ELU (see FIG. 4 and FIG. 5). In other words, the observation image KGB is generated as an image in which a contour of the object, the image of which is picked up by the image pickup unit 111, is emphasized according to the emphasis level ELU.

The image generating unit 122A outputs both of the observation image KGB generated as explained above and the emphasis level ELU used for the generation of the observation image KGB to the endoscopic image processing apparatus 13A.

The image converting unit 131A detects models of the endoscope 11A and the main body apparatus 12A based on the endoscopic information EJB and the main body apparatus information HJB outputted from the main body apparatus 12A.

When detecting based on the endoscopic information EJB and the main body apparatus information HJB outputted from the main body apparatus 12A that, for example, the model of the endoscope 11A is the model EMA and the model of the main body apparatus 12A is the model HMA, the image converting unit 131A performs conversion processing for converting the observation image KGB outputted from the main body apparatus 12A into an image for lesion recognition RGB. A specific example of such conversion processing is explained below with reference to FIG. 4.

The image converting unit 131A performs conversion processing for converting, based on the emphasis level ELU outputted from the main body apparatus 12A and the emphasis level ELD read from the storage medium 134A, the observation image KGB corresponding to the emphasis level ELU into an endoscopic image NGB corresponding to the emphasis level ELD (see FIG. 4). In other words, the endoscopic image NGB is equivalent to an image generated by the image generating unit 122A when the model of the main body apparatus 12A is the model HMA and the emphasis level of the contour emphasis processing is set to 0 (the default emphasis level). The endoscopic image NGB is generated as an image in which the contour of the object, the image of which is picked up by the image pickup unit 111, is not emphasized. Note that when both of the emphasis level ELU and the emphasis level ELD are 0, that is, when the emphasis level ELU and the emphasis level ELD are equal, the image converting unit 131A performs subsequent processing using the observation image KGB as the endoscopic image NGB.

The image converting unit 131A performs conversion processing for converting the endoscopic image NGB into the image for lesion recognition RGB using the emphasis level ELA read from the storage medium 134A (see FIG. 4). In other words, the image for lesion recognition RGB is generated as an image in which a contour of an object included in the endoscopic image NGB is emphasized according to the emphasis level ELA.

The emphasis level ELA for learning image is equivalent to an emphasis level with the highest frequency of use among the emphasis levels ELU set by the user in each of the plurality of past observation images used for the learning for implementing the lesion recognizing function of the lesion recognizing unit 132A. In other words, the emphasis level ELA for learning image is equivalent to an emphasis level with the largest number of times of setting by the user among a plurality of emphasis levels used in the predetermined processing performed at generation of each of the plurality of learning images. Accordingly, with the conversion processing of the image converting unit 131A explained above, emphasis states of the contour of the object in the image for lesion recognition RGB generated according to the observation image KGB obtained in the actual endoscopic observation and the learning image LGA used for the learning for implementing the lesion recognizing function of the lesion recognizing unit 132A can be made similar to each other.

According to the specific example explained above, the image converting unit 131A performs, as conversion processing for converting an observation image into an image for lesion recognition, processing for converting the observation image KGB into the endoscopic image NGB corresponding to the default setting value in the predetermined processing based on the emphasis level ELU for present observation image acquired from the main body apparatus 12A and processing for converting the endoscopic image NGB into the image for lesion recognition RGB corresponding to the emphasis level ELA for learning image.

The lesion recognizing unit 132A performs processing for detecting a lesioned part included in the image for lesion recognition RGB obtained as the processing result of the image converting unit 131A and performs processing for acquiring information concerning the detected lesioned part.

The display control unit 133A generates a display image HGB by combining the observation image KGB outputted from the main body apparatus 12A and the information concerning the lesioned part obtained as a processing result of the lesion recognizing unit 132A and outputs the generated display image HGB to the display apparatus 14 (see FIG. 4).

When detecting based on the endoscopic information EJB and the main body apparatus information HJB outputted from the main body apparatus 12A that, for example, the model of the endoscope 11A is a model EMB different from the model EMA and the model of the main body apparatus 12A is a model HMB different from the model HMA, the image converting unit 131A performs conversion processing for converting the observation image KGB into an image for lesion recognition RGC. A specific example of such conversion processing is explained below with reference to FIG. 5.

The image converting unit 131A performs conversion processing for converting, based on the emphasis level ELU outputted from the main body apparatus 12A and the emphasis level ELD read from the storage medium 134A, the observation image KGB corresponding to the emphasis level ELU into an endoscopic image NGC1 corresponding to the emphasis level ELD (see FIG. 5). In other words, the endoscopic image NGC1 is equivalent to an image generated by the image generating unit 122A when the model of the main body apparatus 12A is the model HMB and the emphasis level of the contour emphasis processing is set to 0 (the default emphasis level). The endoscopic image NGC1 is generated as an image in which the contour of the object, the image of which is picked up by the image pickup unit 111, is not emphasized. Note that when both of the emphasis level ELU and the emphasis level ELD are 0, that is, when the emphasis level ELU and the emphasis level ELD are equal, the image converting unit 131A performs subsequent processing using the observation image KGB as the endoscopic image NGC1.

The image converting unit 131A reads, out of a plurality of matrixes stored in the storage medium 134A, a matrix MAT corresponding to the models EMB and HMB detected based on the endoscopic information EJB and the main body apparatus information HJB.

More specifically, for example, when detecting that the model of the endoscope 11A is the model EMB and the model of the main body apparatus 12A is the model HMB, the image converting unit 131A reads a matrix MATA from the storage medium 134A. The matrix MATA is set as a matrix including a coefficient capable of converting a color tone and resolution of an image acquired by an endoscope system including an endoscope of the model EMB and a main body apparatus of the model HMB into a color tone and resolution of an image acquired by the endoscope system including the endoscope of the model EMA and the main body apparatus of the model HMA.

For example, when detecting that the model of the endoscope 11A is the model EMA and the model of the main body apparatus 12A is the model HMB, the image converting unit 131A reads a matrix MATB from the storage medium 134A. The matrix MATB is set as a matrix including a coefficient capable of converting a color tone and resolution of an image acquired by an endoscope system including the endoscope of the model EMA and the main body apparatus of the model HMB into a color tone and resolution of an image acquired by the endoscope system including the endoscope of the model EMA and the main body apparatus of the model HMA.

For example, when detecting that the model of the endoscope 11A is the model EMB and the model of the main body apparatus 12A is the model HMA, the image converting unit 131A reads a matrix MATC from the storage medium 134A. The matrix MATC is set as a matrix including a coefficient capable of converting a color tone and resolution of an image acquired by an endoscope system including the endoscope of the model EMB and the main body apparatus of the model HMA into a color tone and resolution of an image acquired by the endoscope system including the endoscope of the model EMA and the main body apparatus of the model HMA.

The image converting unit 131A performs conversion processing for converting the endoscopic image NGC1 into an endoscopic image NGC2 by applying the matrix MAT read from the storage medium 134A to an endoscopic image NGC1 (see FIG. 5). In other words, the endoscopic image NGC2 is equivalent to an image obtained by converting a color tone and resolution of the endoscopic image NGC1 to match the endoscope system including the endoscope of the model EMA and the main body apparatus of the model HMA.

The image converting unit 131A performs conversion processing for converting the endoscopic image NGC2 into the image for lesion recognition RGC using the emphasis level ELA read from the storage medium 134A (see FIG. 5). In other words, the image for lesion recognition RGC is generated as an image in which a contour of an object included in the endoscopic image NGC2 is emphasized according to the emphasis level ELA.

The emphasis level ELA for learning image is equivalent to an emphasis level with the highest frequency of use among the emphasis levels ELU set in each of the plurality of past observation images used for the learning for implementing the lesion recognizing function of the lesion recognizing unit 132A. In other words, the emphasis level ELA for learning image is equivalent to an emphasis level with the largest number of times of setting by the user among a plurality of emphasis levels used in the predetermined processing performed at generation of each of the plurality of learning images. Accordingly, with the conversion processing of the image converting unit 131A explained above, emphasis states of the contour of the object in the image for lesion recognition RGC generated according to the observation image KGB obtained in the actual endoscopic observation and the learning image LGA used for the learning for implementing the lesion recognizing function of the lesion recognizing unit 132A can be made similar to each other.

According to the specific example explained above, the image converting unit 131A performs, as conversion processing for converting an observation image into an image for lesion recognition, processing for converting the observation image KGB into the endoscopic image NGC1 corresponding to the default setting value in the predetermined processing based on the emphasis level ELU for present observation image acquired from the main body apparatus 12A, processing for converting the endoscopic image NGC1 into the endoscopic image NGC2, and processing for converting the endoscopic image NGC2 into the image for lesion recognition RGB corresponding to the emphasis level ELA for learning image. According to the specific example explained above, when converting the observation image KGB into an endoscopic image, the image converting unit 131A performs processing that differs according to a combination of the model of the endoscope 11A and the model of the main body apparatus 12A.

The lesion recognizing unit 132A performs processing for detecting a lesioned part included in the image for lesion recognition RGC obtained as the processing result of the image converting unit 131A and performs processing for acquiring information concerning the detected lesioned part.

The display control unit 133A generates a display image HGC by combining the observation image KGB outputted from the main body apparatus 12A and the information concerning the lesioned part obtained as a processing result of the lesion recognizing unit 132A and outputs the generated display image HGC to the display apparatus 14 (see FIG. 5).

As explained above, according to the present embodiment, when the actual endoscopic observation is performed using the endoscope system having the same configuration as the configuration of the endoscope system used for the acquisition of the learning image LGA, the image for lesion recognition RGB having the emphasis state similar to the emphasis state of the learning image LGA is generated by the conversion processing of the image converting unit 131A and the processing relating to the recognition of the lesioned part included in the generated image for lesion recognition RGB is performed by the lesion recognizing unit 132A. As explained above, according to the present embodiment, when the actual endoscopic observation is performed using the endoscope system having the configuration different from the configuration of the endoscope system used for the acquisition of the learning image LGA, the image for lesion recognition RGC having the emphasis state similar to the emphasis state of the learning image LGA is generated by the conversion processing of the image converting unit 131A and the processing relating to the recognition of the lesioned part included in the generated image for lesion recognition RGC is performed by the lesion recognizing unit 132A. Accordingly, according to the present embodiment, it is possible to suppress deterioration in recognition accuracy of a lesioned part that occurs because of a difference between acquisition conditions for an image used for machine learning and an image obtained in the actual endoscopic observation.

Note that, in the present embodiment, the image converting unit 131A may specify any one of the model of the endoscope 11A, the model of the main body apparatus 12A, and the emphasis level ELU by performing processing for recognizing a character string included in the observation image KGB outputted from the main body apparatus 12A.

Third Embodiment

Figure 6:
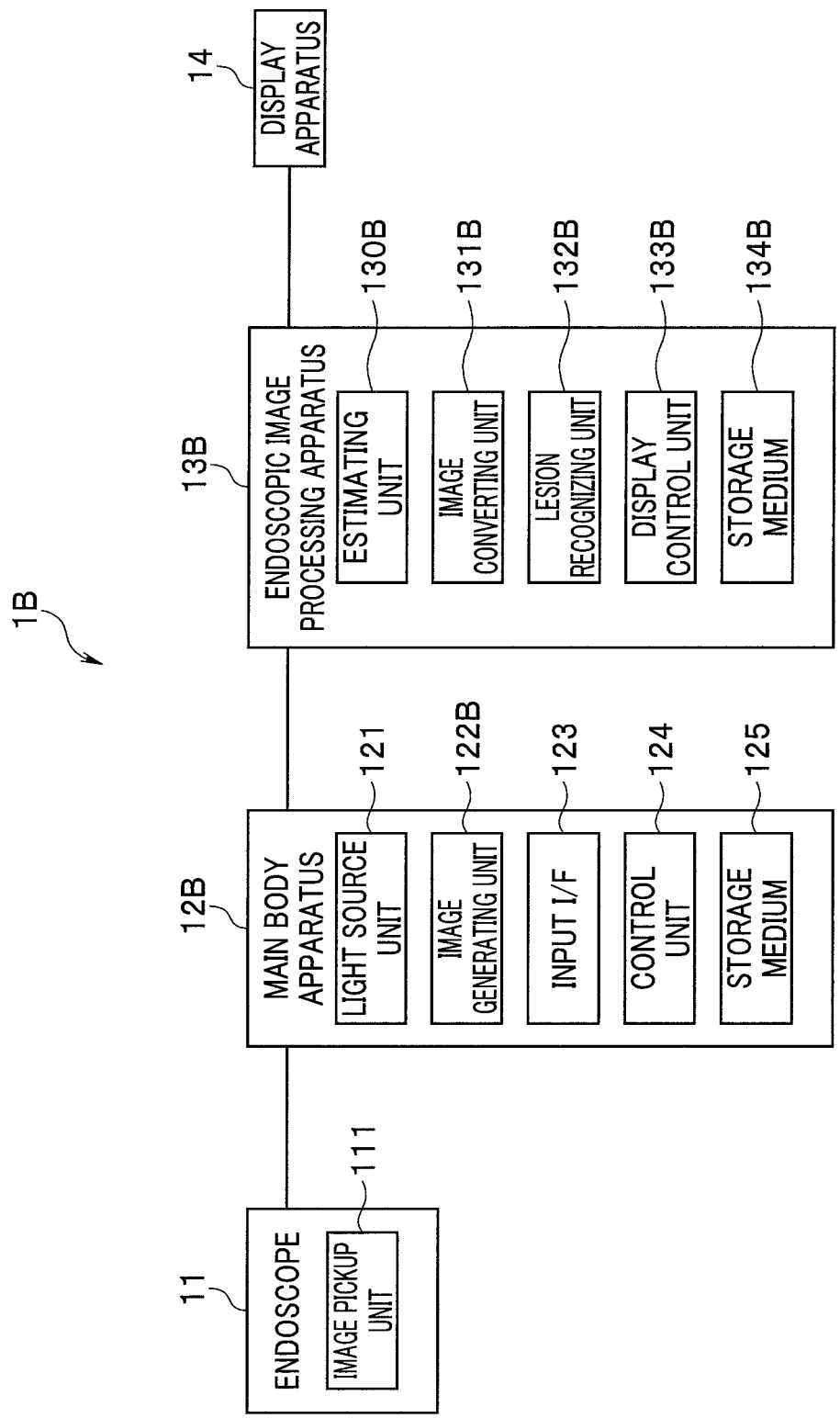
FIG. 6 is a diagram showing a configuration of a main part of an endoscope system including an endoscopic image processing apparatus according to a third embodiment.
Figure 7:
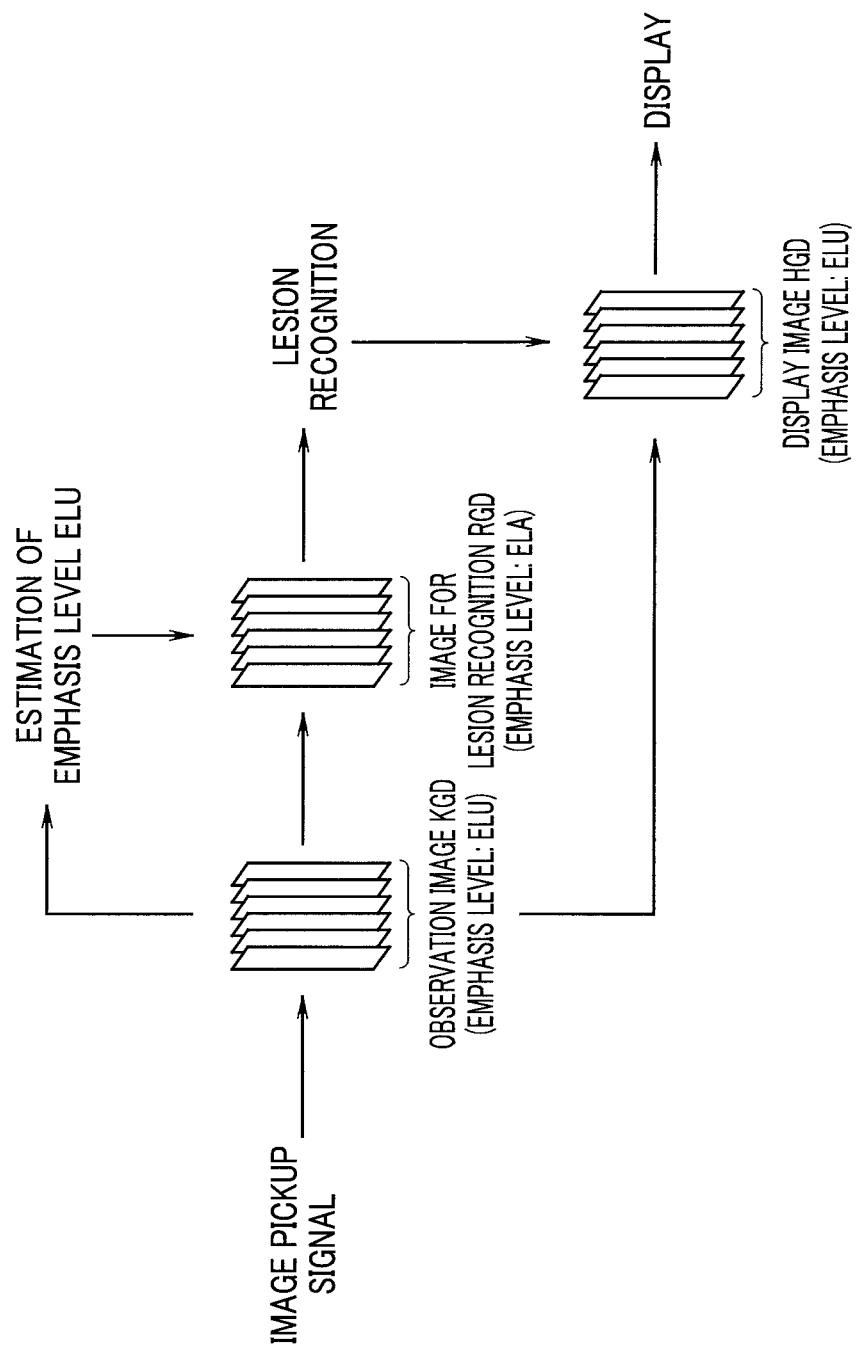
FIG. 7 is a diagram showing an overview of operation performed in the endoscopic image processing apparatus and the like according to the third embodiment.
Figure 8:
FIG. 8 is a diagram showing an example of table data used in processing of the endoscopic image processing apparatus according to the third embodiment.

FIG. 6 to FIG. 8 relate to a third embodiment of the present invention.

Note that, in the present embodiment, detailed explanation concerning portions having the same configurations and the like as the configuration and the like in at least one of the first and second embodiments is omitted as appropriate and portions having configurations and the like different from the configurations and the like in both the first and second embodiments are mainly explained.

An endoscope system 1B includes, as shown in FIG. 6, the endoscope 11, a main body apparatus 12B, an endoscopic image processing apparatus 13B, and the display apparatus 14. FIG. 6 is a diagram showing a configuration of a main part of an endoscope system including an endoscopic image processing apparatus according to the third embodiment.

The main body apparatus 12B is detachably connected to each of the endoscope 11 and the endoscopic image processing apparatus 13B. The main body apparatus 12B includes, for example, as shown in FIG. 6, the light source unit 121, an image generating unit 122B, the input I/F 123, the control unit 124, and the storage medium 125.

The image generating unit 122B is configured to generate an observation image by reading a setting value for present observation image stored in the storage medium 125 and applying predetermined processing to an image pickup signal outputted from the endoscope 11 using the read setting value. The image generating unit 122B is configured to, when detecting that the setting value for present observation image is not stored in the storage medium 125, generate the observation image using, as the setting value for present observation image, a default setting value read from the storage medium 125. The image generating unit 122B is configured to output the observation image generated as explained above to the endoscopic image processing apparatus 13B. Note that, in the present embodiment, the predetermined processing performed by the image generating unit 122B only has to include one or more kinds of processing in which a setting value can be changed by a user.

In the present embodiment, the image generating unit 122B and the control unit 124 of the main body apparatus 12B may be configured as individual electronic circuits or may be configured as circuit blocks in an integrated circuit such as an FPGA (field programmable gate array). In the present embodiment, for example, the main body apparatus 12B may include one or more processors such as CPUs. By modifying a configuration according to the present embodiment as appropriate, for example, a not-shown computer may read, from the storage medium 125, a program for causing the computer to execute the functions of the image generating unit 122B and the control unit 124 and may perform operation corresponding to the read program.

The endoscopic image processing apparatus 13B is detachably connected to each of the main body apparatus 12B and the display apparatus 14. The endoscopic image processing apparatus 13B is configured to receive, from the main body apparatus 12B, an input of an observation image generated by applying predetermined processing to an image pickup signal obtained by picking up an image of an object in a subject with the endoscope 11. The endoscopic image processing apparatus 13B has a lesion recognizing function capable of recognizing a lesioned part included in the inputted observation image. The endoscopic image processing apparatus 13B includes an estimating unit 130B, an image converting unit 131B, a lesion recognizing unit 132B, a display control unit 133B, and a storage medium 134B.

The estimating unit 130B is configured to perform processing for detecting one or more parameters in the observation image outputted from the main body apparatus 12B. The estimating unit 130B is configured to perform estimation processing for estimating, based on the parameters detected from the observation image outputted from the main body apparatus 12B and table data read from the storage medium 134B, a setting value for present observation image used by the image generating unit 122B when generating the observation image.

The image converting unit 131B is configured to perform conversion processing for converting, based on a setting value for observation image obtained as a processing result of the estimating unit 130B and the table data and a setting value of learning images read from the storage medium 134B, the observation image outputted from the main body apparatus 12B into an image for lesion recognition.

The lesion recognizing unit 132B has a lesion recognizing function implemented by performing machine learning with the same method as the method of the lesion recognizing unit 132. The lesion recognizing unit 132B is configured to perform, as processing corresponding to the lesion recognizing function, processing for detecting a lesioned part included in the image for lesion recognition obtained as a processing result of the image converting unit 131B and perform processing for acquiring information concerning the detected lesioned part. In other words, the lesion recognizing unit 132B has a lesion recognizing function implemented by performing machine learning using, as a plurality of learning images, a plurality of past observation images generated through the predetermined processing by the image generating unit 122B.

The display control unit 133B is configured to generate a display image by combining the observation image outputted from the main body apparatus 12B and the information concerning the lesioned part obtained as a processing result of the lesion recognizing unit 132B and output the generated display image to the display apparatus 14. In other words, the display control unit 133B is configured to generate a display image by combining the observation image inputted from the main body apparatus 12B and the information concerning the lesioned part obtained by the lesion recognizing unit 132B applying the processing corresponding to the lesion recognizing function to the image for lesion recognition. The display control unit 133B is configured to, when information concerning the lesioned part is not obtained by the processing of the lesion recognizing unit 132B, directly output the observation image outputted from the main body apparatus 12B to the display apparatus 14 as a display image.

The storage medium 134B includes, for example, a non-volatile memory. In the storage medium 134B, the setting value for learning image equivalent to the past setting value for observation image used for learning for implementing the lesion recognizing function of the lesion recognizing unit 132B is stored. In other words, the setting value for learning image stored in the storage medium 134B is equivalent to the past setting value for observation image used in the predetermined processing performed by the image generating unit 122B and set by the user at generation of each of the plurality of learning images. In the storage medium 134B, the table data used in the estimation processing of the estimating unit 130B and the conversion processing of the image converting unit 131B are stored.

The table data is created as data indicating a relation between parameters detectable from the observation image outputted from the main body apparatus 12B and setting values for observation image corresponding to the parameters.

In the present embodiment, the respective sections of the endoscopic image processing apparatus 13B may be configured as individual electronic circuits or may be configured as circuit blocks in an integrated circuit such as an FPGA (field programmable gate array). In the present embodiment, for example, the endoscopic image processing apparatus 13B may include one or more processors such as CPUs. By modifying the configuration according to the present embodiment as appropriate, for example, a not-shown computer may read, from the storage medium 134B, a program for causing the computer to execute the functions of the estimating unit 130B, the image converting unit 131B, the lesion recognizing unit 132B, and the display control unit 133B and may perform operation corresponding to the read program.

Subsequently, action in the present embodiment is explained with reference to FIG. 7 and FIG. 8. FIG. 7 is a diagram showing an overview of operation performed in the endoscopic image processing apparatus and the like according to the third embodiment. FIG. 8 is a diagram showing an example of table data used in processing of the endoscopic image processing apparatus according to the third embodiment.

In the present embodiment, it is assumed that respective observation images (learning images) used for the learning for implementing the lesion recognizing function of the lesion recognizing unit 132B are acquired by the endoscope system including the endoscope 11 and the main body apparatus 12B.

In the present embodiment, as an example, the same contour emphasis processing as the contour emphasis processing of the image generating unit 122 is performed by the image generating unit 122B. In the explanation of the present embodiment, it is assumed that a setting value of the contour emphasis processing performed by the image generating unit 122B is represented as a plurality of emphasis levels to which numerical values 0 to P (P is an integer equal to or larger than 1) are allocated.

After connecting the respective sections of the endoscope system 1B and turning on a power supply, a user such as a surgeon inserts the insertion section of the endoscope 11 into an inside of a subject and disposes the distal end portion of the insertion section in a position where an image of a desired object can be picked up on the inside of the subject. According to such operation by the user, illumination light is supplied from the light source unit 121 to the endoscope 11 and an image of return light from the object illuminated by the illumination light is picked up by the image pickup unit 111, and an image pickup signal generated by the image pickup unit 111 is outputted to the main body apparatus 12B.

The user operates the input I/F 123 to thereby perform, for example, an instruction for setting the emphasis level used in the contour emphasis processing of the image generating unit 122B to the desired emphasis level ELU. According to such operation by the user, the emphasis level (setting value) for present observation image stored in the storage medium 125 is updated to ELU.

The image generating unit 122B generates an observation image KGD by reading the emphasis level ELU for present observation image stored in the storage medium 125 and applying predetermined processing (including the contour emphasis processing) to an image pickup signal outputted from the endoscope 11 using the read emphasis level ELU (see FIG. 7). In other words, the observation image KGD is generated as an image in which a contour of the object, the image of which is picked up by the image pickup unit 111, is emphasized according to the emphasis level ELU.

The image generating unit 122B outputs the observation image KGD generated as explained above to the endoscopic image processing apparatus 13B.

The estimating unit 130B performs processing for detecting, based on a luminance gradient of the observation image KGD outputted from the main body apparatus 12B, average edge intensity ESA in the observation image. The estimating unit 130B performs estimation processing for estimating, based on the average edge intensity ESA detected from the observation image KGD and table data TDA read from the storage medium 134B, an emphasis level for present observation image used by the image generating unit 122B when generating the observation image KGD.

For example, as shown in FIG. 8, the table data TDA is created as data indicating a relation between the average edge intensity ESA of the observation image KGD and an emphasis level for observation image corresponding to the average edge intensity ESA. In other words, respective emphasis levels included in table data TDA correspond to an emphasis level ELU for present observation image used in the contour emphasis processing performed by the image generating unit 122B when the observation image KGD is generated.

By referring to the table data TDA in FIG. 8, for example, when the average edge intensity ESA detected from the observation image KGD is equal to or larger than 0 and equal to or smaller than ES1, the estimating unit 130B estimates that an emphasis level for observation image used by the image generating unit 122B when generating the observation image KGD is 0. By referring to the table data TDA in FIG. 8, for example, when the average edge intensity ESA detected from the observation image KGD is larger than ES1 and equal to or smaller than ES2, the estimating unit 130B estimates that the emphasis level for observation image used by the image generating unit 122B when generating the observation image KGD is 1.

In other words, the estimating unit 130B performs estimation processing for estimating, based on the table data TDA created as data indicating a relation between the average edge intensity ESA of the observation image KGD and an emphasis level for observation image corresponding to the average edge intensity ESA, an emphasis level for present observation image used in the contour emphasis processing included in the predetermined processing performed when the observation image KGD is generated.

The image converting unit 131B performs conversion processing for converting, based on the emphasis level ELU for observation image obtained as a processing result of the estimating unit 130B and the table data TDA and the emphasis level ELA for learning image read from the storage medium 134B, the observation image KGD outputted from the main body apparatus 12B into an image for lesion recognition RGD (see FIG. 7).

More specifically, for example, when the emphasis level ELU for observation image obtained as the processing result of the estimating unit 130B is 0 and the emphasis level ELA for learning image read from the storage medium 134B is 1, the image converting unit 131B generates the image for lesion recognition RGD by performing conversion processing for increasing, based on the table data TDA in FIG. 8, the average edge intensity ESA of the observation image KGD to predetermined average edge intensity ESB belonging to a range of an average edge intensity larger than ES1 and equal to or smaller than ES1. In other words, when the emphasis level ELU for observation image obtained as the processing result of the estimating unit 130B is lower than the emphasis level ELA for learning image, the image converting unit 131B generates the image for lesion recognition RGD by performing conversion processing for increasing the average edge intensity ESA of the observation image KGD based on the table data TDA.

For example, when the emphasis level ELU for observation image obtained as the processing result of the estimating unit 130B is 1 and the emphasis level ELA for learning image read from the storage medium 134B is 0, the image converting unit 131B generates the image for lesion recognition RGD by performing conversion processing for reducing, based on the table data TDA in FIG. 8, the average edge intensity ESA of the observation image KGD to predetermined average edge intensity ESC belonging to a range of average edge intensity equal to or larger than 0 and equal to or smaller than ES1. In other words, when the emphasis level ELU for observation image obtained as the processing result of the estimating unit 130B is higher than the emphasis level ELA for learning image, the image converting unit 131B generates the image for lesion recognition RGD by performing conversion processing for reducing the average edge intensity ESA of the observation image KGD based on the table data TDA.

For example, when the emphasis level ELU for observation image obtained as the processing result of the estimating unit 130B is 1 and the emphasis level ELA for learning image read from the storage medium 134B is 1, the image converting unit 131B acquires the observation image KGD as the image for lesion recognition RGD. In other words, when the emphasis level ELU for observation image obtained as the processing result of the estimating unit 130B and the emphasis level ELA for learning image are equal, the image converting unit 131B acquires the observation image KGD as the image for lesion recognition RGD without performing the conversion processing for increasing or reducing the average edge intensity ESA of the observation image KGD.

The emphasis level ELA for learning image is equivalent to an emphasis level with the highest frequency of use among the emphasis levels ELU set by the user in each of the plurality of past observation images used for the learning for implementing the lesion recognizing function of the lesion recognizing unit 132B. Accordingly, with the estimation processing of the estimating unit 130B and the conversion processing of the image converting unit 131B explained above, emphasis states of the contour of the object in the image for lesion recognition RGD generated according to the observation image KGD obtained in the actual endoscopic observation and the learning image LGA used for the learning for implementing the lesion recognizing function of the lesion recognizing unit 132B can be made similar to each other.

The lesion recognizing unit 132B performs processing for detecting a lesioned part included in the image for lesion recognition RGD obtained as the processing result of the image converting unit 131B and performs processing for acquiring information concerning the detected lesioned part.

The display control unit 133B generates a display image HGD by combining the observation image KGD outputted from the main body apparatus 12 and the information concerning the lesioned part obtained as the processing result of the lesion recognizing unit 132B and outputs the generated display image HGD to the display apparatus 14 (see FIG. 7).

As explained above, according to the present embodiment, the image for lesion recognition RGD having the emphasis state similar to the emphasis state of the learning image LGA is generated by the estimation processing of the estimating unit 130B and the conversion processing of the image converting unit 131B. Processing relating to recognition of the lesioned part included in the generated image for lesion recognition RGD is performed by the lesion recognizing unit 132B. Accordingly, according to the present embodiment, it is possible to suppress deterioration in recognition accuracy of a lesioned part that occurs because of a difference between acquisition conditions for an image used for machine learning and an image obtained in the actual endoscopic observation.

In the present embodiment, for example, the table data TDB created as data indicating a relation between an average luminance value of the observation image KGD and a brightness level corresponding to the average luminance value and a brightness level BLA for learning image may be stored in the storage medium 134B.

Note that respective brightness levels included in the table data TDB correspond to a brightness level BLU for present observation image used in brightness adjustment processing performed by the image generating unit 122B when the observation image KGD is generated. The brightness level BLU for present observation image is represented as, for example, numerical values −K to +K (K is an integer equal to or larger than 1) and is set to a desired level corresponding to operation of the input I/F 123 by the user. The brightness level BLA for learning image is equivalent to a brightness level with the highest frequency of use among brightness levels BLU set in each of a plurality of past observation images used for the learning for implementing the lesion recognizing function of the lesion recognizing unit 132B.

In the case explained above, estimation processing for estimating the brightness level BLU for present observation image used in the brightness adjustment processing based on the table data TDB is performed by the estimating unit 130B. In the case explained above, conversion processing for converting the observation image KGD into the image for lesion recognition RGD based on the brightness level BLU for present observation image obtained as a processing result of the estimating unit 130B, the table data TDB, and the brightness level BLA for learning image is performed by the image converting unit 131B. Accordingly, in the case explained above, it is possible to generate the image for lesion recognition RGD having brightness similar to brightness of the learning image LGA.

In the present embodiment, for example, table data TDC created as data indicating a relation between average pixel values of respective color components (blue, green, and red color components) included in the observation image KGD, color tone levels corresponding to the average pixel values of the respective color components and a color tone level CLA for learning image may be stored in the storage medium 134B.

Note that the respective color tone levels included in the table data TDC correspond to a color tone level CLU for present observation image used in the color tone adjustment processing performed by the image generating unit 122B when the observation image KGD is generated. The color tone level CLU for present observation image is represented as, for example, numerical values −L to +L (L is an integer equal to or larger than 1) and is set to a desired level corresponding to operation of the input I/F 123 by the user. The color tone level CLA for learning image is equivalent to a color tone level with the highest frequency of use among color tone levels CLU set in each of a plurality of past observation images used for the learning for implementing the lesion recognizing function of the lesion recognizing unit 132B.

In the case explained above, the estimation processing for estimating the color tone level CLU for present observation image used in the color tone adjustment processing based on the table data TDC is performed by the estimating unit 130B. In the case explained above, the conversion processing for converting the observation image KGD into the image for lesion recognition RGD based on the color tone level CLU for present observation image obtained as the processing result of the estimating unit 130B, the table data TDC, and the color tone level CLA for learning image is performed by the image converting unit 131B. Accordingly, in the case explained above, it is possible to generate the image for lesion recognition RGD having a color tone similar to a color tone of the learning image LGA.

What is claimed is:

1. An endoscopic image processing apparatus to which an image generated by applying predetermined processing to an image pickup signal obtained by picking up an image of an object in a subject with an endoscope is inputted from an external apparatus, the endoscopic image processing apparatus having a lesion recognizing function capable of recognizing a lesioned part included in the inputted image, the endoscopic image processing apparatus comprising a processor, the processor having the lesion recognizing function implemented by performing machine learning using, as a plurality of learning images, a plurality of past observation images generated through the predetermined processing, the processor performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

2. The endoscopic image processing apparatus according to claim 1, wherein the past setting value for observation image is set by a user.

3. The endoscopic image processing apparatus according to claim 1, wherein the setting value for learning image is equivalent to a setting value with a largest number of times of setting by a user among a plurality of setting values used in the predetermined processing performed at generation of each of the plurality of learning images.

4. The endoscopic image processing apparatus according to claim 1, wherein, when the image inputted from the external apparatus is an endoscopic image generated using a default setting value in the predetermined processing, the processor performs, as the conversion processing, processing for converting the endoscopic image into the image for lesion recognition corresponding to the setting value for learning image.

5. The endoscopic image processing apparatus according to claim 1, wherein, when the image inputted from the external apparatus is a present observation image generated by performing the predetermined processing using a setting value for present observation image set by a user, the processor performs, as the conversion processing, processing for converting the present observation image into an endoscopic image corresponding to a default setting value in the predetermined processing based on the setting value for present observation image acquired from the external apparatus and processing for converting the endoscopic image into the image for lesion recognition corresponding to the setting value for learning image.

6. The endoscopic image processing apparatus according to claim 5, wherein, when converting the present observation image into the endoscopic image, the processor performs processing that differs according to a combination of a model of the endoscope and a model of the external apparatus.

7. The endoscopic image processing apparatus according to claim 6, wherein the processor specifies at least one of a model of the endoscope and a model of the external apparatus by performing processing for recognizing a character string included in the present observation image.

8. The endoscopic image processing apparatus according to claim 1, wherein
when the image inputted from the external apparatus is a present observation image generated by performing the predetermined processing using a setting value for present observation image set by a user, the processor performs estimation processing for estimating the setting value for present observation image based on table data indicating a relation between parameters detectable from the present observation image and setting values for observation image corresponding to the parameters, and
the processor performs, as the conversion processing, processing for converting the present observation image into the image for lesion recognition based on the setting value for present observation image obtained as the estimation processing result, the table data, and the setting value for learning image.

9. The endoscopic image processing apparatus according to claim 8, wherein the processor performs estimation processing for estimating, based on the table data created as data indicating a relation between average edge intensity of the present observation image and an emphasis level for observation image corresponding to the average edge intensity, an emphasis level for present observation image used in contour emphasis processing included in the predetermined processing performed when the present observation image is generated.

10. The endoscopic image processing apparatus according to claim 8, wherein the processor performs estimation processing for estimating, based on the table data created as data indicating a relation between average luminance of the observation image and a brightness level for observation image corresponding to the average luminance, a present brightness level for observation image used in brightness adjustment processing included in the predetermined processing performed when the present observation image is generated.

11. The endoscopic image processing apparatus according to claim 8, wherein the processor performs estimation processing for estimating, based on the table data created as data indicating a relation between average pixel values of respective color components included in the observation image and color tone levels for observation image corresponding to the average pixel values of the respective color components, a color tone level of present observation image used in color tone adjustment processing included in the predetermined processing performed when the present observation image is generated.

12. The endoscopic image processing apparatus according to claim 1, wherein the processor generates a display image by combining the image inputted from the external apparatus and information concerning the lesioned part obtained by applying the processing corresponding to the lesion recognizing function to the image for lesion recognition.

13. An endoscopic image processing method in an endoscopic image processing apparatus to which an image generated by applying predetermined processing to an image pickup signal obtained by picking up an image of an object in a subject with an endoscope is inputted from an external apparatus, the endoscopic image processing apparatus having a lesion recognizing function capable of recognizing a lesioned part included in the inputted image,
the endoscopic image processing method comprising:
performing machine learning for implementing the lesion recognizing function using, as a plurality of learning images, a plurality of past observation images generated through the predetermined processing; and
performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

14. A non-transitory computer-readable recording medium recording a program to be executed by a computer to which an image generated by applying predetermined processing to an image pickup signal obtained by picking up an image of an object in a subject with an endoscope is inputted from an external apparatus, the computer having a lesion recognizing function capable of recognizing a lesioned part included in the inputted image,
the recording medium recording a program for causing the computer to execute:
a step of performing machine learning for implementing the lesion recognizing function using, as a plurality of learning images, a plurality of past observation images generated through the predetermined processing; and a step of performing conversion processing for converting, based on a setting value for learning image equivalent to a past setting value for observation image used in the predetermined processing performed at generation of each of the plurality of learning images, the image inputted from the external apparatus into an image for lesion recognition used for processing corresponding to the lesion recognizing function.

* * * * *